US007109379B2

United States Patent
Sato et al.

(10) Patent No.: US 7,109,379 B2
(45) Date of Patent: Sep. 19, 2006

(54) METHOD FOR PRODUCING CARBONYL COMPOUND

(75) Inventors: Kazuhiko Sato, Ibaraki (JP); Youko Usui, Ibaraki (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/523,366

(22) PCT Filed: Jul. 24, 2003

(86) PCT No.: PCT/JP03/09377

§ 371 (c)(1),
(2), (4) Date: Sep. 16, 2005

(87) PCT Pub. No.: WO2004/014830

PCT Pub. Date: Feb. 19, 2004

(65) Prior Publication Data

US 2006/0106250 A1 May 18, 2006

(30) Foreign Application Priority Data

Aug. 9, 2002 (JP) ............................ 2002-233501

(51) Int. Cl.
C07C 45/00 (2006.01)
C07C 51/00 (2006.01)
(52) U.S. Cl. .................. 568/322; 568/361; 568/403; 568/430; 568/485; 562/418; 562/519; 562/538
(58) Field of Classification Search .................. None
See application file for complete search history.

(56) References Cited

U.S. PATENT DOCUMENTS

| 4,218,401 A | 8/1980 | Wymore ..................... 568/402 |
| 4,480,135 A | 10/1984 | Esposito et al. ............ 568/385 |
| 6,232,505 B1 | 5/2001 | Law .......................... 568/385 |

FOREIGN PATENT DOCUMENTS

| EP | 39111 A1 | 11/1981 |
| EP | 102655 A1 | 3/1984 |

OTHER PUBLICATIONS

R. Anderson et al., "Selective Oxidation of Alcohols to Carbonyl Compounds and Carboxylic Acids With Platinum Group Metal Catalysts," Advanced Synthesis & Catalysis, 345(4), pp. 517-523, 2003.
S. Martin et al., "Efficient Solvent-free iron (III) catalyzed oxidation of alcohols by hydrogen peroxide," Tetrahedron Letters, 44, pp. 549-552, 2003.

*Primary Examiner*—Sikarl A. Witherspoon
(74) *Attorney, Agent, or Firm*—Morgan, Lewis & Bockius LLP

(57) ABSTRACT

An oily solution of water-insoluble aliphatic alcohol is allowed to react with an aqueous hydrogen peroxide solution in the presence of a catalyst containing a metal compound belonging to Group 8 to 10 of the Periodic Table in a heterogeneous solution system. As a result, a carbonyl compound can be produced from an aqueous hydrogen peroxide solution under mild conditions in high yield. Also, the reaction operation is simple and easy, a step for removing solvent after completion of the reaction is not necessary and influence and toxicity upon the environment and human body are markedly small. Thus, a carbonyl compound can be produced safely, simply and efficiently.

5 Claims, No Drawings

METHOD FOR PRODUCING CARBONYL COMPOUND

TECHNICAL FIELD

This application is the national stage of PCT/JP03/09377, filed Jul. 24, 2003, and published as WO 04/014830 on Feb. 19, 2004.

The present invention relates to a method for producing a carbonyl compound which is useful as an intermediate of various organic compounds. More particularly, the present invention relates to a novel method for producing a carbonyl compound by a reaction of an oily solution of water-insoluble alcohol with an aqueous hydrogen peroxide solution.

BACKGROUND OF THE INVENTION

As methods for producing a carbonyl compound by oxidizing alcohol, known are reactions using high valence chromium (*Comprehensive Organic Synthesis;* 1st ed.; B. M. Trost and I. Fleming, Ed.; Pergamon: Oxford, 1991; Vol. 7, pp. 251–289), manganese compounds (M. Hudlicky, *Oxidations in Organic Chemistry;* ACS Monograph Ser. 186; American Chemical Society: Washington, D.C., 1990), a high valence iodine compound (*J Org. Chem.*, 1983, 48, 4155–4156), N-methylmorpholine N-oxide in the presence of a ruthenium catalyst (*J. Chem. Soc. Chem. Commun.*, 1987, 1625–1627) and the like as the oxidizing agent. However, it is hard to say that these methods are industrially superior methods because of the large load on the environment in terms of the generation of by-products having high toxicity, corrosiveness of the oxidizing agents and the like.

On the other hand, it can be said that oxygen and hydrogen peroxide are excellent oxidizing agents in industrially applying them due to small environmental load, because they are inexpensive and have no corrosiveness, and there is no by-product after the reaction or it is harmless water.

As a method for producing a carbonyl compound from alcohol by using oxygen as the oxidizing agent, a method using a catalyst carrying a metal of Group 8 to 10 as the catalyst has been known (U.S. Pat. No. 4,218,401 specification), but this method requires a high temperature of 225 to 600° C.

On the other hand, as a method for producing a carbonyl compound from alcohol by using hydrogen peroxide as the oxidizing agent, a method using a catalyst carrying a metal of Group 8 to 10 as the catalyst has been reported (U.S. Pat. No. 6,232,505 specification), but the substrate is limited to water-soluble 1-methoxy-2-propanol which forms a homogenous phase with an aqueous hydrogen peroxide solution. In addition, the substrate must be used by preparing into a 20 wt % aqueous solution.

Also, an oxidation reaction of alcohol by using an aqueous hydrogen peroxide solution in which titanium silicate (TS-1) is used as the catalyst is known too (U.S. Pat. No. 4,480,135 specification), but in the oxidation reaction of water-insoluble alcohol, it is essential to use a polar organic solvent such as acetone for preparing a uniform solution by dissolving an oil solution of alcohol in an aqueous hydrogen peroxide solution. As a result, the reaction operation and apparatus become complex because of the necessity to employ a means for removing the polar organic solvent at the time of the isolation of a carbonyl compound as the product of interest. In addition, influence and toxicity of the polar organic solvent itself upon the environment and human body have been pointed out.

DISCLOSURE OF THE INVENTION

The present invention has been made for the purpose of solving the above-described problems involved in the related art, and its object is to provide a safe, convenient and efficient novel method for the production of carbonyl compounds by a reaction of an oily solution of water-insoluble alcohol with an aqueous hydrogen peroxide solution, by which a carbonyl compound can be obtained in high yield from the oily solution of water-insoluble alcohol under mild reaction conditions, wherein the reaction operation is simple and easy, a step of removing a solvent after completion of the reaction is not necessary, and influence and toxicity upon the environment and human body are markedly small.

In order to solve the above-described problems, the present inventors have conducted intensive studies and found as a result that, when a reaction using a heterogeneous solution system of an aqueous hydrogen peroxide solution with an oily solution of water-insoluble alcohol is selected instead of the conventional reaction method in which the oxidation reaction is carried out in a homogeneous solution system of a polar solvent solution of an oily solution of water-insoluble alcohol and an aqueous hydrogen peroxide solution, the corresponding carbonyl compound can be produced safely and conveniently in high yield which is different from the conventional commonplace technical knowledge, thus resulting in the accomplishment of the present invention. According to the present invention, an oily solution of a carbonyl compound as the intended product is easily separated from the aqueous hydrogen peroxide solution after the reaction.

That is, according to the present invention, the following inventions are provided.

(1) A method for producing a carbonyl compound, which comprises reacting an oily solution of water-insoluble aliphatic alcohol with an aqueous hydrogen peroxide solution in the presence of a catalyst containing a metal compound belonging to Group 8 to 10 of the Periodic Table in a heterogeneous solution system.

(2) The method according to the above-described (1), wherein the water-insoluble aliphatic alcohol is saturated aliphatic secondary alcohol, and the carbonyl compound is ketone.

(3) The method according to the above-described (1), wherein the water-insoluble aliphatic alcohol is saturated aliphatic primary alcohol, and the carbonyl compound is aldehyde or carboxylic acid.

(4) The method according to any one of the above-described (1) to (3), wherein the catalyst containing a metal compound belonging to Group 8 to 10 of the Periodic Table is a zero-valent metal catalyst.

(5) The method according to any one of the above-described (1) to (4), wherein the zero-valent metal catalyst is platinum/carbon, platinum black, bis(dibenzylideneacetone)platinum, palladium/carbon, rhodium/carbon or ruthenium/carbon.

BEST MODE FOR CARRYING OUT THE INVENTION

The method of the present invention for producing a carbonyl compound by the oxidation reaction of water-insoluble aliphatic alcohol using hydrogen peroxide is characterized in that the oxidation reaction is carried out in a heterogeneous solution of an aqueous hydrogen peroxide solution and an oily solution of alcohol in the presence of a catalyst containing a metal compound belonging to Group 8 to 10 of the Periodic Table.

Conventionally, in the case of a liquid-liquid reaction, when substrates themselves or the materials and reaction reagents such as an oxidizing agent and a reaction accelerator do not have compatibility, it has been considered that a process in which a homogenous solution of the materials and a reaction reagent is prepared in advance by using a solvent capable of mutually dissolving them for smooth reaction, and then the reaction is carried out is advantageous from the points of selectivity, yield and the like.

As described above, this idea is also followed in the case of the carbonyl compound synthesis reaction through the reaction of alcohol with hydrogen peroxide, and a process in which a carbonyl compound is produced by allowing a uniform solution of an aqueous solution of water-soluble alcohol and an aqueous hydrogen peroxide solution to react in the presence of a catalyst of a metal belonging to Group 8 to 10 of the Periodic Table has been employed in the present invention described in U.S. Pat. No. 6,232,505 specification. In addition, a process in which a carbonyl compound is produced by preparing a homogenous solution of an oily solution of alcohol and hydrogen peroxide in advance by using a polar solvent such as acetone, and allowing this homogenous solution to react in the presence of a titanium silicate (TS-1) catalyst has been employed in the present invention described in U.S. Pat. No. 4,480,135 specification.

From the viewpoint of carrying out such an oxidation reaction more efficiently while taking protection of the environment and human body into consideration, the present inventors have carried out various studies and experiments and theoretical discussions and found as a result that, when this oxidation reaction of water-insoluble aliphatic alcohol is carried out by using hydrogen peroxidase as the oxidizing agent in a heterogeneous solution system of an oily solution of water-insoluble alcohol and an aqueous hydrogen peroxide solution, which is different from the case of a homologous solution system like the conventional technical common knowledge, it forms the carbonyl compound in good yield and considerably contributes to the reduction of environmental load. Such a knowledge cannot be expected at all by the conventional technical common sense but is a phenomenon found by the present inventors through continuous efforts of experiments and studies.

The carbonyl compound which is obtained by the method of the present invention includes ketone, aldehyde and carboxylic acid, and they are dependent on the kind of aliphatic alcohol as the substrate. That is, ketone is obtained when aliphatic secondary alcohol is used as the substrate, and aldehyde or carboxylic acid is obtained when aliphatic primary alcohol is used as the substrate.

Examples of the secondary alcohol as the substrate of the present invention include 2-pentanol, 3-pentanol, 2-hexanol, 3-hexanol, 2-heptanol, 3-heptanol, 4-heptanol, 2-octanol, 3-octanol, 4-octanol, 6-methyl-5-hepten-2-ol, 2-nonanol, 3-nonanol, 4-nonanol, 5-nonanol, 2-decanol, 3-decanol, 4-decanol, 5-decanol, 11-dodecen-2-ol, cyclobutanol, cyclopentanol, cyclohexanol, cycloheptanol, cyclooctanol, cyclododecanol, 2-methylcyclohexanol, 3-methylcyclohexanol, 4-methylcyclohexanol, 2-tert-butylcyclohexanol, 3-tert-butylcyclohexanol, 4-tert-butylcyclohexanol, menthol, 1,7,7-trimethylbicyclo[2,2,1]heptan-2-ol, 5-cyclohexadecenol, 1,2-cyclohexanediol, 1,4-cyclohexanediol, 1-phenylethanol, 1-(2-fluorophenyl)ethanol, 1-(3-fluorophenyl)ethanol, 1-(4-fluorophenyl)ethanol, 1-(4-chlorophenyl)ethanol, 1-(4-bromophenyl)ethanol, 1-(4-methoxyphenyl)ethanol, 1-(4-methoxycarbonylphenyl)ethanol, 1-(4-acetylphenyl)ethanol, 1-phenylpropanol and the like.

The secondary alcohol preferably used in the present invention is saturated aliphatic secondary alcohol.

Examples of primary alcohol as the substrate include 1-pentanol, 1-hexanol, 1-heptanol, 1-octanol, 1-nonanol, 1-decanol, 2-methyl-1-hexanol, 3-methyl-1-hexanol, 4-methyl-1-hexanol, 5-methyl-1-hexanol, 2-ethyl-1-hexanol, 3-ethyl-1-hexanol, 4-ethyl-1-hexanol, 5-ethyl-1-hexanol, 2,2-dimethyl-1-propanol, 1,2-epoxy-10-decanol, benzyl alcohol, 2-fluorobenzyl alcohol, 3-fluorobenzyl alcohol, 4-fluorobenzyl alcohol, 4-chlorobenzyl alcohol, 4-bromobenzyl alcohol, 4-methoxybenzyl alcohol, 4-methoxycarbonylbenzyl alcohol, 4-acetylbenzyl alcohol, 4-cyanobenzyl alcohol, 2-phenylethanol and the like. The primary alcohol preferably used in the present invention is saturated aliphatic primary alcohol.

According to the present invention, as described above, its object is to provide a safe, convenient and efficient method for the production of a carbonyl compound by a reaction of aliphatic alcohol with an aqueous hydrogen peroxide solution, by which a carbonyl compound can be obtained in high yield from water-insoluble aliphatic alcohol under mild reaction conditions, wherein the reaction operation is simple and easy, a step of removing a solvent after completion of the reaction is not necessary and influence and toxicity upon the environment and human body are markedly small, so that an oily solvent solution of aliphatic alcohol dissolved in a non-polar solvent such as hydrocarbon having no compatibility with eater can be exemplified as the oily solution of aliphatic alcohol, in addition to an oily solution of an aliphatic alcohol itself, but it is most preferable to use an oily solution of aliphatic alcohol itself in view of the above-described environmental load reduction and solvent-removing operation.

In the case of the production of ketone, an amount of hydrogen peroxide to be used is within the range of usually 1.0 to 3 moles, preferably 1.0 to 1.3 moles, based on the hydroxyl group of secondary alcohol. In the case of the production of aldehyde or carboxylic acid, it is within the range of usually 1.0 to 10 moles, preferably from 1.0 to 2.6 moles, based on the hydroxyl group of primary alcohol. A concentration of hydrogen peroxide has no particular limitation and a commercially available 30% aqueous solution may be sufficient enough, but it may be used after dilution.

As the catalyst containing a metal compound belonging to Group 8 to 10 of the Periodic Table, a carrying metal, a metal powder or a metal complex of these metals can be used, but a so-called zero-valent metal catalyst is preferably used. Examples of the catalyst include platinum/carbon, platinum/silica, platinum/alumina, platinum black, bis(dibenzylideneacetone)platinum, bis(1,5-cyclooctadiene)platinum, palladium/carbon, palladium/silica, palladium/alumina, palladium black, tris(benzylideneacetone)dipalladium, nickel/carbon, nickel/silica, nickel/alumina, nickel powders, nickel black, rhodium/carbon, rhodium/silica, rhodium/alumina, rhodium black, cobalt powders, ruthenium/carbon, ruthenium/silica, ruthenium/alumina, ruthenium black and the like, and platinum/carbon, platinum black, bis(dibenzylideneacetone)platinum, palladium/carbon, rhodium/carbon and ruthenium/carbon are preferred. The zero-valent metal catalyst of Group 8 to 10 should be used alone or as a mixture of two or more. The used amount is within the range of usually 0.0001 to 10% by mol, preferably 0.0005 to 5% by mol, based on the substrate alcohol.

Although reaction conditions of the method of the present invention are not particularly limited, the reaction is carried out within the range of usually 30 to 120° C., preferably 50 to 100° C. The reaction pressure may be ordinary pressure, pressurization or reduced pressure, but the reaction is preferably carried out under ordinary pressure.

According to the preferable production method of the present invention, a method in which a solution prepared by mixing an oily solution of water-insoluble aliphatic alcohol and a catalyst is heated to the reaction-carrying temperature, and then the mixture is allowed to react under stirring by gradually adding dropwise an aqueous hydrogen peroxide solution.

As described above, the carbonyl compound obtained by the method of the present invention includes ketone, aldehyde or carboxylic acid.

Examples of the ketone include 2-pentanone, 3-pentanone, 2-hexanone, 3-hexanone, 2-heptanone, 3-heptanone, 4-heptanone, 2-octanone, 3-octanone, 4-octanone, 6-methyl-5-hepten-2-one, 2-nonanone, 3-nonanone, 4-nonanone, 5-nonanone, 2-decanone, 3-decanone, 4-decanone, 5-decanone, 11-dodecen-2-one, cyclobutanone, cyclopentenone, cyclohexanone, cycloheptanone, cyclooctanone, cyclododecanone, 2-methylcyclohexanone, 3-methylcyclohexanone, 4-methylcyclohexanone, 2-tert-butylcyclohexanone, 3-tert-butylcyclohexanone, 4-tert-butylcyclohexanone, menthone, camphor, 5-cyclohexadecenone, 1,2-cyclohexanedione, 1,4-cyclohexanedione, acetophenone, o-fluoroacetophenone, m-fluoroacetophenone, p-fluoroacetophenone, p-chloroacetophenone, p-bromoacetophenone, p-methoxyacetophenone, p-acetylacetophenone, p-cyanoacetophenone, propiophenone and the like.

Examples of the aldehyde include pentanal, hexanal, heptanal, octanal, nonal, decanal, 2-methylhexanal, 3-methylhexanal, 4-methylhexanal, 5-methylhexanal, 2-ethylhexanal, 3-ethylhexanal, 4-ethylhexanal, 5-ethylhexanal, tert-butylacetaldehyde, 9,10-epoxydecanal, benzaldehyde, o-fluorobenzaldehyde, m-fluorobenzaldehyde, p-fluorobenzaldehyde, p-chlorobenzaldehyde, p-bromobenzaldehyde, p-methoxybenzaldehyde, p-methoxycarbonylbenzaldehyde, p-acetylbenzaldehyde, p-cyanobenzaldehyde, phenylacetaldehyde and the like.

Examples of the carboxylic acid include pentanoic acid, hexanoic acid, heptanoic acid, octanoic acid, nonanoic acid, decanoic acid, 2-methylhexanoic acid, 3-methylhexanoic acid, 4-methylhexanoic acid, 5-methylhexanoic acid, 2-ethylhexanoic acid, 3-ethylhexanoic acid, 4-ethylhexanoic acid, 5-ethylhexanoic acid, 2,2-dimethylpropanoic acid, 9,10-epoxydecanoic acid, benzoic acid, o-fluorobenzoic acid, m-fluorobenzoic acid, p-fluorobenzoic acid, p-chlorobenzoic acid, p-bromobenzoic acid, p-methoxybenzoic acid, p-methoxycarbonylbenzoic acid, p-acetylbenzoic acid, p-cyanobenzoic acid, phenylacetic acid and the like.

The thus formed carboxylic acid of interest can be purified by separating from the water phase after completion of the reaction, followed by general methods such as recrystallization, distillation and sublimation.

The catalyst can be easily separated by generally used separation operations such as filtration or decantation of the reaction solution, and the recovered catalyst can be used repeatedly as such by washing with water.

EXAMPLES

The present invention is described below in detail based on Examples, but the present invention is not restricted by these Examples.

Example 1

Platinum black (19.5 mg, 0.10 mmol) and 2-octanol (1.6 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 2 hours, and then the reaction solution was cooled to room temperature. As a result of measurement by GLC, it was found that 2-octanone was obtained in yield of 100%.

Comparative Example 1

The reaction was carried out in the same manner as in Example 1, except that 2-octanol and an aqueous hydrogen peroxide solution were made into a homogenous phase by adding dioxane (10 ml) in advance, and 2-octanone was obtained in yield of 37%.

Example 2

Platinum black (1.50 g, 7.7 mmol) and 2-octanol (100 g, 768 mmol) were mixed and stirred at 90° C. for 10 minutes. A 30% aqueous hydrogen peroxide solution (104 g, 918 mmol) was gradually added dropwise to the mixed solution, followed by stirring at 90° C. for 20 hours, and then the reaction solution was cooled to room temperature. The organic phase was separated and washed with 100 ml of a saturated aqueous sodium thiosulfate solution, followed by distillation, and 2-octanone was obtained in yield of 95% (93.9 g, 730 mmol).

Example 3

Platinum black (19.5 mg, 0.100 mmol) and 2-octanol (1.6 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 5 hours, and then the mixed solution was cooled to room temperature. Platinum black was collected from the reaction solution by filtration and washed with 5 ml of water 5 times, and then 2-octanol (1.6 ml, 10 mmol) was added thereto, followed by stirring at 90° C. for 10 minutes. A 30% aqueous hydrogen peroxide solution (1.3 ml, 12 mmol) was gradually added dropwise to the mixed solution, followed by stirring at 90° C. for 5 hours, and then the reaction solution was cooled to room temperature. As a result of measurement by GLC, it was found that 2-octanone was obtained in yield of 91% by the first reaction, and 90% by the second reaction.

Example 4

3%-Platinum/carbon (platinum 0.10 mmol) and 2-octanol (1.6 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 5 hours, and then the reaction solution was cooled to room temperature. As a result of measurement by GLC, it was found that 2-octanone was obtained in yield of 91%.

Example 5

Platinum black (19.5 mg, 0.100 mmol) and 6-methyl-5-hepten-2-ol (1.5 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 15 hours, and then the reaction solution was cooled to room temperature. As a result of measurement by GLC, it was found that 6-methyl-5-hepten-2-one was obtained in yield of 55%.

Example 6

Platinum black (19.5 mg, 0.100 mmol) and cyclohexanol (1.0 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 2 hours, and then the reaction solution was cooled to room temperature. As a result of measurement by GLC, it was found that cyclohexanone was obtained in yield of 94%.

Example 7

Platinum black (19.5 mg, 0.100 mmol) and trans-1,2-cyclohexanediol (1.16 g, 10 mmol) were mixed and stirred at 90° C. for 10 minutes. A 30% aqueous hydrogen peroxide solution (2.6 ml, 23 mmol) was gradually added dropwise to the mixed solution, followed by stirring at 90° C. for 20 hours, and then the reaction solution was cooled to room temperature. As a result of measurement by GLC, it was found that 1,2-cyclohexanedione was obtained in yield of 51%.

Example 8

Platinum black (19.5 mg, 0.100 mmol) and 1-phenylethanol (1.2 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 15 hours, and then the reaction solution was cooled to room temperature. As a result of measurement by GLC, it was found that acetophenone was obtained in yield of 100%.

Example 9

Platinum black (19.5 mg, 0.100 mmol) and 1-octanol (1.6 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 5 hours, and then the reaction solution was cooled to room temperature. As a result of measurement by GLC, it was found that 1-octanal was obtained in yield of 18%, and 1-octanoic acid was obtained in yield of 19%.

Example 10

Platinum black (19.5 mg, 0.100 mmol) and benzyl alcohol (1.0 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 15 hours, and then the reaction solution was cooled to room temperature. As a result of measurement by GLC, it was found that benzaldehyde was obtained in yield of 85%. Benzoic acid was obtained in yield of 0.7%.

Example 11

Platinum black (19.5 mg, 0.100 mmol) and 2-butyl alcohol (0.92 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 2 hours, and then the reaction solution was cooled to room temperature. As a result of measurement by GLC, it was found that 2-butanone was obtained in yield of 100%.

Example 12

Platinum black (19.5 mg, 0.100 mmol) and 2-hexanol (1.3 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 2 hours, and then the reaction solution was cooled to room temperature. As a result of measurement by GLC, it was found that 2-hexanone was obtained in yield of 94%.

Example 13

Platinum black (19.5 mg, 0.100 mmol) and cycloheptanol (1.2 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 2 hours, and then the reaction solution was cooled to room temperature. As a result of measurement by GLC, it was found that cycloheptanone was obtained in yield of 99%.

Example 14

Bis(dibenzylideneacetone)platinum (66.4 mg, 0.100 mmol) and 2-octanol (1.6 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 15 hours, and then the reaction solution was cooled to room temperature. As a result of measurement by GLC, it was found that 2-octanone was obtained in yield of 37%.

Example 15

A 3% palladium/carbon (palladium 0.10 mmol) and 2-octanol (1.6 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 5 hours, and then the reaction solution was cooled to room temperature. As a result of measurement by GLC, it was found that 2-octanone was obtained in yield of 49%.

Example 16

A 5% rhodium/carbon (rhodium 0.10 mmol) and 2-octanol (1.6 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 5 hours, and then the reaction solution was cooled to room temperature. As a result of measurement by GLC, it was found that 2-octanone was obtained in yield of 39%.

Example 17

A 5% ruthenium/carbon (ruthenium 0.10 mmol) and 2-octanol (1.6 ml, 10 mmol) were mixed and stirred at 90° C. for 10 minutes. A 30% aqueous hydrogen peroxide solution (1.3 ml, 12 mmol) was gradually added dropwise to the mixed solution, followed by stirring at 90° C. for 5 hours, and then the reaction solution was cooled to room temperature. As a result of measurement by GLC, it was found that 2-octanone was obtained in yield of 51%.

INDUSTRIAL APPLICABILITY

According to the production method of the present invention, a useful carbonyl compound broadly used as an intermediate of various organic compounds can be obtained under mild conditions in high yield.

In addition, since the method of the present invention does not use an organic solvent, acid and base, the reaction operation is simple and easy, a step of removing solvent after completion of the reaction is not necessary, influence and toxicity upon the environment and human body are markedly small and it also has the effect to reduce load on the environment, so tat carbonyl compounds can be produced safely, conveniently and efficiently. Thus, it can be said that the method of the present invention is an invention which produces industrially great effects.

What is claimed is:

1. A method for producing a carbonyl compound, which comprises reacting an oily solution of water-insoluble aliphatic alcohol with an aqueous hydrogen peroxide solution in the presence of a catalyst containing a metal compound belonging to Group 8 to 10 of the Periodic Table in a heterogeneous solution system.

2. The method according to claim 1, wherein the water-insoluble aliphatic alcohol is saturated aliphatic secondary alcohol, and the carbonyl compound is ketone.

3. The method according to claim 1, wherein the water-insoluble aliphatic alcohol is saturated aliphatic primary alcohol, and the carbonyl compound is aldehyde or carboxylic acid.

4. The method according to claim 1, wherein the catalyst containing a metal compound belonging to Group 8 to 10 of the Periodic Table is a zero-valent metal catalyst.

5. The method according to claim 1, wherein the zero-valent metal catalyst is platinum/carbon, platinum black, bis(dibenzylideneacetone)platinum, palladium/carbon, rhodium/carbon or ruthenium/carbon.

* * * * *